US00PP09133P

United States Patent [19]

Mak

[11] Patent Number: Plant 9,133

[45] Date of Patent: May 9, 1995

[54] LILIUM 'MEMPHIS'

[76] Inventor: Johan A. Mak, 5595 Halls Ferry Rd., Independence, Oreg. 97351

[21] Appl. No.: 314,071

[22] Filed: Sep. 28, 1994

[51] Int. Cl.[6] ..... A01H 5/00

[52] U.S. Cl. ..... Plt./87.4

[58] Field of Search ..... Plt. 87.4

*Primary Examiner*—James R. Feyrer

[57] ABSTRACT

A new variety of hybrid lily plant bearing flowers of excellent form and long persistence, both on the plant and as cut-flowers. The flowers of the new plant are particularly characterized by their deep pink pink coloration shading into a wide white area surrounding a small yellow ray extending from the nectary furrows. This combination is completely new in the Oriental hybrid divisions of lilies suited to forcing and to mass commercial cultivation. The variety is highly resistant to fusarium disease and shows tolerance of virus. The bulbs may be precooled and forced for cut-flower production. The clone is vigorous and is a good grower and propagator.

1 Drawing Sheet

BACKGROUND OF THE INVENTION

My new variety of lily plant originated as a seedling which first flowered in 't Zand, Netherlands, in 1987. The breeding efforts had as their objective the production of large-flowered Oriental hybrids in bicolored combinations of pink, white, and yellow, with pigmented papillae, suited to forcing into flower out of season, heretofore unknown in the lily breeding art.

I achieved the desired objective by intercrossing selected semi-upright pink Oriental seedlings suited to forcing for year-round use as cut-flowers and carrying the recessive gene for a yellow band.

The flowers of my new lily are characterized by large size and broad-tepalled "bowl-shaped" form, unusually thick substance, and deep pink coloration shading into a wide white area which surrounds a small yellow ray extending from the nectaries along the midrib, accented with deeper magenta-rose papillae on the basal half of the tepals, unique among Oriental hybrid lilies. It possesses unusually strong, stout stems. In addition, the clone possesses to a high degree desirable characteristics of hybrid vigor. The clone is a good grower and propagator, as observed at 't Zand, Netherlands, and at Salem, Oreg.

My new variety of lily plant has been asexually reproduced by me and under my direction at 't Zand, Netherlands, and at Salem, Oreg. Successive generations produced by natural propagation from bulblets, by bulb scale propagation, and by tissue culturing from bulb scale explants have demonstrated that the novel and distinctive characteristics of my new variety are fixed and hold true under asexual propagation from generation to generation.

DESCRIPTION OF THE DRAWING

My new variety of lily plant is illustrated in the accompanying photographic drawings, which shows the open bloom in full color and illustrates the flower form, the tepal arrangement, and in particular the novel and distinctive flower coloration, with wide deep pink edges shading into an equally wide white area surrounding a short, narrow yellow ray extending from the nectaries, accented by deeper magenta rose papillae on the basal half of each tepal.

DESCRIPTION OF THE NEW VARIETY

The following is a detailed description of my new variety of Oriental hybrid lily, with nomenclature according to the *International Lily Register* (Royal Horticultural Society of London, Second Edition, 1969), and with color designations according to the Colour Chart of the Royal Horticultural Society, published by the Society in 1966.

THE PLANT

Origin: Seedling.

Seed parent: Selected unnamed Oriental hybrid seedling.

Pollen parent: Selected unnamed Oriental hybrid seedling.

Commercial classification: Hybrid *Lilium* clone.

Horticultural classification: Division VII-B, bowl-shaped Oriental hybrid lily, according to the Horticultural Classification of Lilies, Royal Horticultural Society of London.

Form: Single stem, erect and stately.

Height: 75 to 135 cm from bulbs 14 to 18 cm in circumference, provided their light levels are adequate; low light levels may cause "stretching."

Growth: Vigorous and upright.

Foliage quantity: Abundant.

Size of leaf: Unusually broad, 4 to 7 cm wide × 10 to 14 cm long.

Shape of leaf: Lanceolate (pointed).

Texture: Leathery and glossy.

Color: Medium green, lighter on lower side.

Bulb size: Any size, ranging to 25 cm circumference commercially.

Bulb color: White, with flushes of pink or yellow after exposure to light.

THE BUD

Form: Obtuse, ovoid, and long.

Size: 8 to 11 cm long and 8 to 12 cm in circumference just prior to opening.

Opening: Bud opens slowly, in response to morning light; this takes about one hour.

Color: Soft pink (RHS 66 D-68 D) with ivory white to pale green midribs. Peduncle: Averages 4 to 6 cm, but it may elongate if light levels are too low or if bulbs have been improperly stored prior to forcing. Color is medium green with very light plum overlay.

THE FLOWER

Blooming habit: Annually in midseason; flowers once and profusely.

Size: Flowers are medium large-sized, averaging 13 to 17 cm in diameter, reflexing at the tips on the second day to 12 to 15 cm in diameter. The tepals are broad: outer tepals are 2.25 to 3 cm wide, and the inner tepals are 4.25 to 5 cm wide.

Borne: In a single racemic inflorescence producing 5 to 10 flowers from a bulb 14 to 16 cm in circumference.

Shape: Form a broad bowl shape by the second day after opening, with the "bowl" 10 cm deep.

Tepalage: Typical of genus *Lilium,* with 6 imbricated tepals.

Tepal color: Deep pink (RHS CC red-purple 64 C-D to 68 B-C, depending upon growing temperatures and light levels) in an area 1–1.25 cm wide along tepal margins, decreasing near the base. The pink area shades into a white area which is broader at the base, averaging 2 cm wide about one-third of the tepal length from the base, narrowing to end at the point where the tepal recurves, about one-third of the tepal length from the tips. The white area surrounds a small yellow ray averaging 0.5 to 1.0 cm wide of RHS CC 6 C to 9 C, extending 2 to 4 cm from the green nectaries. The pink color is slightly affected by temperature and light levels; it decreases with high temperatures and low light levels.

Tepal spotting: The basal half of each tepal is spotted with magenta rose papillae of moderate size.

Tepal longevity: Tepals stay on stems about three weeks.

Pedicel length: Average 8 to 12 cm long.

Pedicel color: Medium green with very light plum overlay.

Pedicel form: Sturdy and ascending.

Color changes: Flowers become slightly lighter and a more lavender-toned pink as the flowers age. Low light levels and extreme heat may cause the pink pigmentation to decrease.

Appearance: Flower is shiny.

Disease resistance: The flower and plant are resistant to disease; in particular, they are resistant to Fusarium bulb rot and Botrytis blight.

Fragrance: Light sweet fragrance.

Lasting quality: The flower is long lasting, both on the plant and as a cut-flower.

THE REPRODUCTIVE ORGANS

Stamens: Arrangement typical of genus *Lilium.* Six stamens with soft green to palest pink filaments 7 to 9 cm long.

Pollen and anthers (dehisced): RHS CC greyed red 178A to 181A.

Pistil: One in number, 7 to 9 cm long.

Stigma: Soft greenish-white, large in size.

Characteristics of ovary: Characteristic of genus *Lilium.*

THE FRUIT

Fertility: The fruit bears fertile seed.

Shape: Ovoid.

Color at maturity: Soft brown, sometimes overlaid with soft plum.

My new variety of Oriental hybrid lily most nearly resembles 'Egypt,' but it has more outfacing flowers, a deeper pink coloration, a wide white area in the center of each tepal, and a smaller, less noticeable yellow ray extending from the nectaries. Its tepal margins are also much less ruffled.

I claim:

1. A new and distinctive variety of Oriental hybrid lily plant substantially as herein shown and described, characterized by its high resistance to disease; its tolerance of virus; its vigorous growth and rapid natural propagation; the excellence of its flower form, size, and substance; its versatility both as a garden plant and as a cut-flower producer from pre-cooled bulbs forced under glass out of season; and in particular by its unique upright to semi-upright flowers with deep pink coloration shading into a wide white center bording a short, narrow yellow ray along the midrib, accented with noticeable magneta rose papillae on the basal half of each tepal, a combination unique among Oriental hybrid lilies suited to forcing and to mass commercial cultivation.

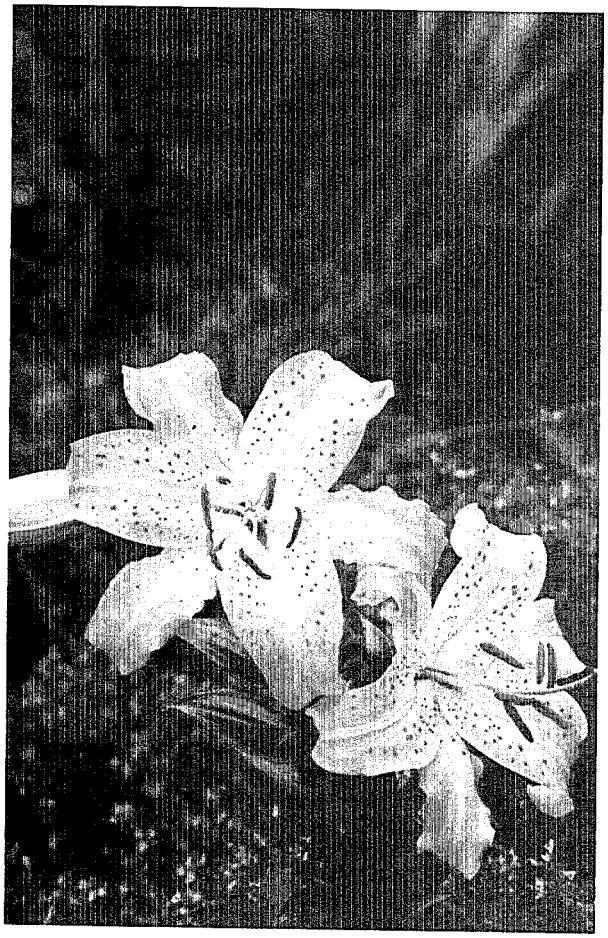

* * * * *